United States Patent [19]

Harandi et al.

[11] Patent Number: 5,015,782
[45] Date of Patent: May 14, 1991

[54] ETHER PRODUCTION

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 495,667

[22] Filed: Mar. 19, 1990

[51] Int. Cl.$^5$ .............................................. C07C 41/06
[52] U.S. Cl. ..................................................... 568/697
[58] Field of Search ......................................... 568/697

[56] References Cited

U.S. PATENT DOCUMENTS 4,714,787 12/1987 Bell et al. .............................. 568/697

Primary Examiner—Howard T. Mars
Attorney, Agent, or Firm—Alexander J. McKillop; Charles J. Speciale; L. G. Wise

[57] ABSTRACT

A process for preparing lower molecular weight unsymmetrical ethers such as methyl t-butyl (MTBE) and t-amyl methyl ether (TAME) from an iso-olefin and methanol, the process comprising a preliminary step of contacting the iso-olefin and methanol with a medium-pore zeolite conversion catalyst in at least one reaction zone under conditions sufficient to convert the iso-olefin and methanol to an unsymmetrical ether and then feeding effluent from the preliminary step to an etherification reaction zone containing a macroreticular polystyrenesulfonic acid resin catalyst.

28 Claims, 1 Drawing Sheet

ETHER PRODUCTION

FIELD OF THE INVENTION

The present invention relates to a multi-stage process and apparatus for preparing unsymmetrical tertiary ethers in high yield and purity. More particularly it relates to a process and apparatus for protection of a highly sensitive polystyrenesulfonic acid resin catalyst used in preparing ethers, such as methyl t-butyl ether (MTBE) and t-amyl methyl ether (TAME).

BACKGROUND OF THE INVENTION

Recent efforts have been made in the field of gasoline blending to increase gasoline octane performance without the addition of deleterious components such as tetraethyl lead and benzene. It has been found that lower molecular weight unsymmetrical ethers such as MTBE and TAME can be added to $C_5$-$C_{10}$ hydrocarbon-containing gasoline products in order to increase octane number. The research octane number (RON) of MTBE has been listed at 115 (Lander, E P. et al, "National Petroleum Refiners Association Annual Meeting", San Francisco, Calif., Mar. 20-24, 1983). The blending octane number of MTBE has been calculated over various concentrations and some of the readings are: RON, 115-135; MON (motor octane number), 98-110; and (RON & MON)/2, 106-122.5 (Pecci, G. et al, *Hyrocarbon Processing*, 1977, 56, 98). Blending octane number rises when MTBE concentration is decreased and saturates concentration of the base fuel is increased.

Conventional etherification processing uses as catalyst a macroreticular cation exchange resin in the hydrogen form. An example of such a catalyst is "Amberlyst 15". A resin catalyst gives a high conversion rate but is unstable at elevated temperatures (above about 90° C.). When overheated, the resin catalyst releases sulfonic and sulfuric acids. In addition leaching of acid substances from the resin catalyst even at normal operating temperatures causes a reverse reaction—decomposition of ether products to starting materials—to occur upon distillation of ether product. Overall yield is thereby significantly decreased (see Takesono et al U.S. Pat. No. 4,182,913).

Etherification reactions conducted over a resin catalyst such as "Amberlyst 15" are usually conducted in the liquid phase below a temperature of about 90° C. and at a pressure of about 200 psig. Equilibrium is more favorable at lower temperatures but the reaction rate decreases significantly. Also excess methanol appears to be required to achieve acceptable selectivity over "Amberlyst 15" (see Chu et al, *Industrial Engineering and Chemical Research*, Vol. 26, No. 2, 1987, 365-369).

Some recent efforts in the field of etherification reactions have focused on the use of acid medium-pore zeolite catalyst for highly selective conversion of iso-olefin and alcohol starting materials. Examples of such zeolite catalysts are ZSM-4, ZSM-5. ZSM-11, ZSM-12, ZSM-23, ZSM-35, ZSM-50 and zeolite Beta. Due to lower acidity as compared to resin catalysts, the zeolites need to be employed at higher reaction temperature to achieve the desired conversion rates. These solid acid catalyst particles are much more thermally stable than resin catalyst, are less sensitive to methanol-to-isobutene ratio, give no acid effluent, and are easily and quickly regenerated (see Chu et al, "Preparation of Methyl tert-Butyl Ether (MTBE) over Zeolite Catalysts", *Industrial Engineering and Chemical Research*, op cit.).

It is an object of the present invention to provide a process and apparatus for continuous operation in preparation of t-alkyl ethers from an alcohol and an iso-olefin with a conventional acid resin catalyst whereby the resin catalyst is protected from impurities such as nitrogen compounds, metals, and coke.

SUMMARY OF THE INVENTION

In one of its aspects, the present invention comprises a multistage process for etherifying a mixed $C_4^+$ olefinic hydrocarbon feedstock containing isoalkenes. The multistage process comprises contacting olefinic feedstock and aliphatic alcohol in a first reaction stage under partial etherification conditions with a regenerable inorganic metal oxide acid solid catalyst to convert a major amount of the isoalkene to $C_5^+$ tertiary-alkyl ether. A reaction effluent is recovered from the first stage, the reaction effluent containing ether product, unreacted alcohol and unreacted olefin including isoalkene. The first stage reaction effluent is charged to a second stage catalytic distillation column containing solid acid resin etherification catalyst in a plurality of fixed bed catalysis-distillation zones. In the second stage substantially full etherification of the isoalkene is completed. A liquid product containing $C_5^+$ ethers is recovered from the catalytic distillation column.

The first stage solid catalyst can be regenerated to remove feedstock impurity and coke and to restore acid activity. Reactivated catalyst can be returned to the first stage for continued ether production. Regeneration of a metal oxide catalyst such as ZSM-5 is considerably more cost effective than purifying a contaminated acid resin catalyst.

DRAWING

The single FIGURE is a schematic diagram of a preferred embodiment of the present process, showing major operating units and flow of reactants and chemical products.

DETAILED DESCRIPTION OF THE INVENTION

Figure 1:
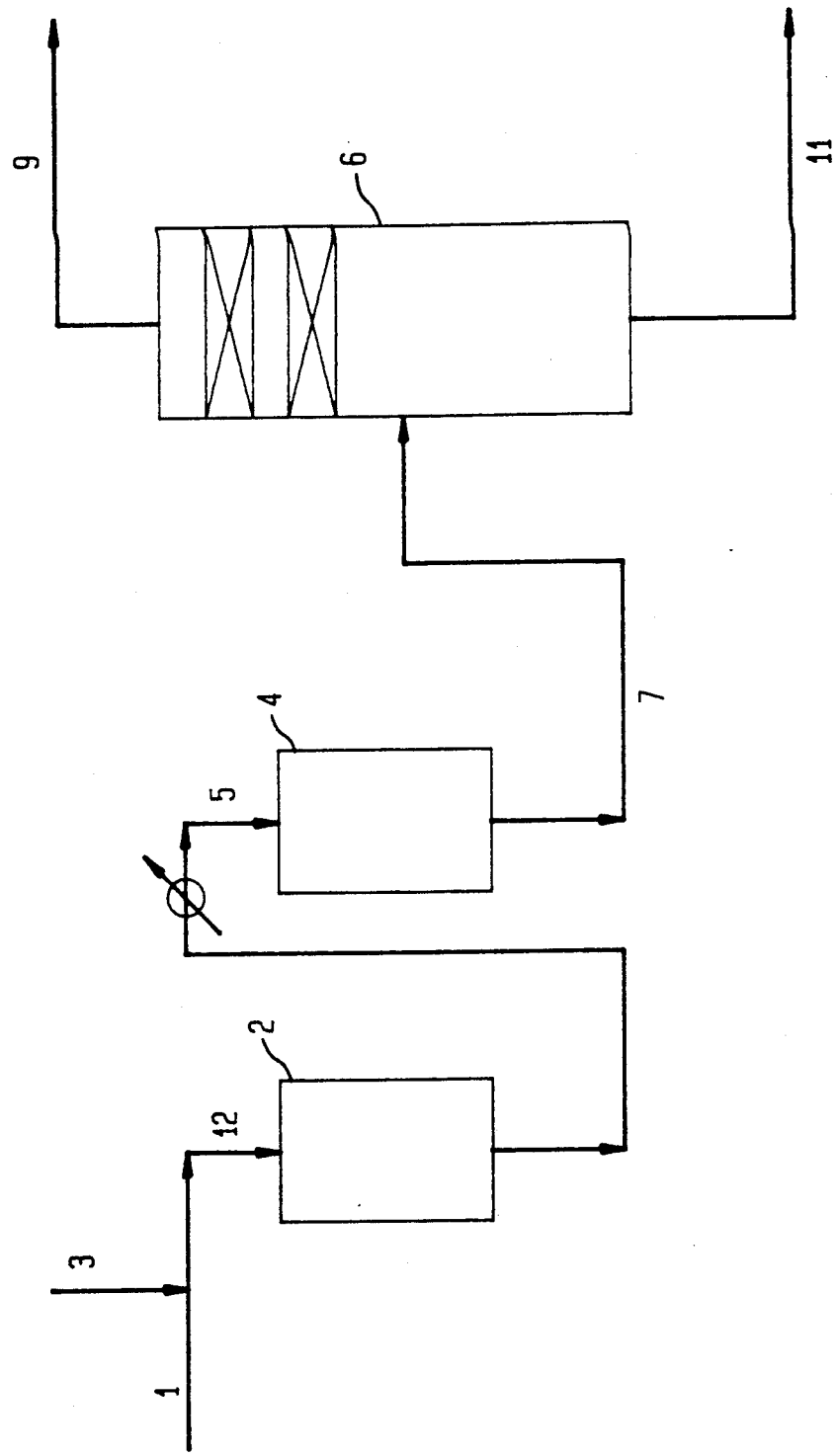

In a preferred embodiment, the present inventive process relates to the preparation of MTBE wherein selectivity and yield are increased and destruction of resin catalyst is greatly decreased. Two reaction zones are maintained in series arrangement. A first reaction zone contains solid crystalline acid medium-pore metallosilicate catalyst particles. A second reaction zone contains acid resin catalyst. Mixed feedstock containing methanol and isobutene-containing $C_4$ hydrocarbons is contacted with solid catalyst particles in the first reaction zone under etherification conditions to obtain an intermediate product comprising MTBE and unreacted feedstock. The intermediate product is then withdrawn from the first reaction zone and added to the second zone for contact with acid resin catalyst under etherification conditions. A product containing a major amount of MTBE is then withdrawn from the second reaction zone. The product is fractionated to obtain a purified MTBE which is recovered.

In this description, metric units and parts by weight are employed unless otherwise stated.

The preferred present process further comprises removing the first reaction zone from on-line contact with the feedstock, regenerating the solid catalyst particles in the first reaction zone, and resuming addition of feedstock to the first reaction zone. The preferred solid acid catalyst particles are aluminosilicate zeolites selected from ZSM-5, ZSM-11, ZSM-50 and zeolite Beta. Since the mixed olefinic feedstock contains many impurities, even after treatment in a "Merox" unit and a water wash, the solid acid zeolite catalyst becomes highly contaminated after a period of on-line contact with feedstock. Some of the impurities which are absorbed on the zeolite particles are: nitrogen compounds; metals such as Al, Fe, Na and Mg; and oligomers of olefins and diolefins, such as isoprene and cyclopentadiene. Diolefinic compounds and other related hydrocarbons are deposited as coke on the surface and interstices of the zeolite and/or resin catalytic particles. It is therefore an objective of the present process to remove feedstock impurities in the first reaction zone concurrently with the preparation of ethers.

The first reaction zone preferably comprises a plurality of catalytic fixed bed reactors operatively connected for swing from production mode to regeneration mode in alternating sequence. A continuous operation is thus maintained when a fixed bed must be removed from service for catalyst to be regenerated. In one embodiment of the process, the first reaction zone comprises at least three catalytic fixed bed reactors whereby two reactors remain operative at all times. Thus iso-olefin-containing feedstock and alcohol contact acid medium-pore zeolite catalyst in a sequential fashion in the first reaction zone.

In an alternative embodiment, the first reaction zone contains reactors other than fixed bed, such as moving bed, slurry, fluidized bed, or ebullated bed. It is within the scope of the present process and apparatus to adjust the number and types of reactors which contain acid zeolite catalyst in order to optimize both product yield and overall energy consumption as would be practiced by one skilled in the art.

Catalyst regeneration can be achieved by contacting contaminated zeolite catalyst particles with oxygen or oxygen-containing gas in a regeneration zone under conditions of temperature and pressure sufficient to remove at least a major amount of impurities from the catalyst particles. Typical oxidative regeneration conditions are 700°-950° F. and 0-200 psig. In an alternative embodiment zeolite catalyst particles can be regenerated by stripping with a hot stream of hydrogen gas at a temperature of about 700° F. to 1000° F. Hydrogen stripping avoids the problem of inactivating the catalyst by "steaming" which can occur under oxidative regeneration conditions due to water formation.

Since zeolite catalyst particles are readily regenerated, the mixed olefinic feedstock can contain a significant amount of impurities. If desired, the step of washing the feedstream with water can be eliminated. Isobutene-containing feedstreams of low quality can be employed in resin-catalyzed etherification reactions if said feedstreams are first contacted with zeolite catalytic particles such as ZSM-5 under conditions of the present process.

The second reaction zone contains an acid resin catalyst which is preferably a macroreticular polystyrene sulfonic acid resin catalyst. In a preferred embodiment the second reaction zone contains a catalytic distillation column containing polystyrenesulfonic acid resin catalyst in a plurality of fixed bed catalysis-distillation units located in the upper half of the distillation column. The reaction section column is preferably operated at a temperature about 10° to 30° C. lower than the temperature of the first reaction zone.

In an alternate embodiment, the second reaction zone is not a catalytic distillation column, but rather a single reactor or plurality of reactors. Reactor configuration can take many forms, for example, fixed bed, stirred slurry (see Lee U.S. Pat. No. 3,940,450, incorporated herein by reference), swing or ebullated bed. It is within the scope of the present process to employ for the second reaction zone any reactor configuration for sequencing acceptable to the skilled engineer. The present invention contemplates that an acid resin catalyst be employed following a regenerable etherification catalyst, preferably in the second reaction zone. In a preferred embodiment, the resin catalyst is "Amberlyst 15".

The present process is an improvement in the conventional process for producing an ether by reacting an olefinic feedstock with an alcohol. The conventional reaction is conducted in the presence of a solid etherification catalyst of the sulfonic resin type in acid form and the olefinic feedstock contains impurities which substantially reduce the activity of the resin catalyst.

The improvement of the present process comprises adding a preliminary step of contacting the olefin and alcohol reactants in the liquid phase with oxidatively regenerable solid acid catalyst particles in a preliminary reaction zone under partial etherification conditions to produce an intermediate stream comprising tert-alkyl ether and unreacted olefin and alcohol, said intermediate stream being substantially free from impurities which reduce catalyst activity. In a preferred embodiment the olefinic feedstock comprises isobutene in an amount of at least about 10 wt. %. Preferably the acid catalyst is aluminosilicate having the structure of ZSM-5 or zeolite Beta and is contained in a swing reactor or slurry type reactor for ease of removal from contact with reactants. Once removed from on-line activity, the acid catalyst is easily regenerated at elevated temperature.

Although the preferred alcohol is methanol, suitable substitutes include ethanol or isopropanol (isopropyl alcohol). Of course, use of these substitutes will yield different ether products. It is within the scope of the present process to employ a mixture of lower molecular weight alcohols. Although isobutene is the preferred hydrocarbon feed, other iso-olefin such as 3-methyl-2-butene can be etherified in the present process.

An apparatus for catalytically preparing ethers from olefins and alcohols is presently disclosed. The apparatus comprises a first reaction zone comprising an inlet means for receiving a mixed feedstock comprising olefins and alcohols, a reactor system containing solid acid medium-pore zeolite catalyst particles, and an outlet means for withdrawing intermediate product comprising ethers and unreacted feedstock. Said apparatus further comprises a secondary reaction zone comprising an inlet means for receiving withdrawn intermediate product, a catalytic distillation column containing solid acid resin etherification catalyst in a plurality of fixed bed catalysis distillation zones, and an outlet means for withdrawing a final etherification product. Also included in the apparatus is a means for transferring intermediate product from the first reaction zone to the second reaction zone.

Referring to the FIGURE, a pre-washed C$_4$ hydrocarbon feedstock which can contain impurities is combined as by line 1 with a lower molecular weight alcohol feed which passes through line 3. The combined stream enters reaction zone 2 as by line 12. A regenerable solid metal oxide acid catalyst such as ZSM-5 is contained in reaction zone 2. The mixed alcoholic $C_4$ hydrocarbon feedstream contacts the solid catalyst within the reaction zone 2 at predetermined reaction zone conditions of temperature and pressure to convert at least a portion of the feedstream to MTBE. Impurities present within the feedstock are effectively removed from the partially converted feedstream by the solid acid catalyst.

A first intermediate stream containing MTBE and unreacted $C_4$ hydrocarbons and alcohol is cooled before entering reaction zone 4 as by line 5. Reaction zone 4 contains a solid regenerable metal oxide acid catalyst such as ZSM-5. The first intermediate stream contacts solid catalyst under etherification conditions to obtain MTBE. Any impurities contained in the first intermediate stream are adsorbed by the solid catalyst.

Regeneration of the solid acid catalyst in both reaction zones 2 and 4 is accomplished by procedures well-known in the art. A series of swing reactors can be employed, whereby a reactor containing contaminated de-activated catalyst can be easily removed from the process and replaced immediately with a reactor containing active catalyst. Reaction zones 2 and 4 can be serially arranged catalytic fixed bed reactors or combined into a single moving bed, slurry, or ebullated bed reaction zone. The catalytic material, preferably ZSM-5, can be regenerated by contact with oxygen or an oxygen-containing gas at elevated temperatures.

A second intermediate stream containing MTBE and unreacted $C_4$ hydrocarbons and alcohol is withdrawn from reaction zone 4 and enters catalytic distillation column 6 as by line 7. In a preferred embodiment, the temperature of second intermediate stream is reduced prior to entering the distillation column. In distillation column 6 a substantial portion of unreacted $C_4$ hydrocarbons and alcohols are converted to MTBE over a polystyrenesulfonic acid resin catalyst such as "Amberlyst 15". Etherification over resin catalyst is carried out preferably at a temperature of about 37° to 75° C. and a pressure of about 10 to 350 psig. In a preferred embodiment acid resin catalyst is placed in the rectifying section of a debutanizer column used for stabilizing the ethers. A product stream comprising MTBE can be withdrawn from distillation column 6 by line 11. Unreacted light gases are removed as by line 9.

To illustrate the common problem of catalyst poisoning when a polysulfonic acid resin catalyst is employed in the etherification process, MTBE resin catalyst unit is operated in a continuous fashion for a period of six months. Isobutene containing hydrocarbon feed is purified in a "Merox" unit and water-washed prior to entering the MTBE reactor. Conversion decreases from 93% to 52% during the six month period. Analysis identifies the contaminants on the resin catalyst. The major contaminants are nitrogen compounds, which are responsible for about 60% of the catalyst deactivation. The concentration of nitrogen on the deactivated resin catalyst is about $25 \times 10^3$ ppm. Metals such as Al, Fe, Na and Mg account for about 10% of the deactivation. The source of such metals is mainly from the water wash tower. The concentration of the metals on the deactivated catalyst is about $15 \times 10^2$ ppm. The third type of contaminant is coke. Coke is formed on the resin catalyst due to the presence of such compounds as cyclopentadiene and isoprene in the hydrocarbon feedstock.

Continuous monitoring of the feedstock is necessary to control particularly the diolefinic $C_5$ hydrocarbon content. One of the advantages of the present process is that coke formation occurs primarily on the zeolite catalyst. Oxidative regeneration or hydrogen stripping of zeolite catalyst can then effectively remove the coke and nonmetallic contaminants from the etherification catalyst.

It is also observed that acetone and nitrile compounds were major contaminants in the hydrocarbon feedstocks which have been water washed. For example, a feed sample may contain 190 ppm acetone, 3 ppm acetonitrile and 16 ppm propionitrile. An advantage of the present process is that the hydrocarbon feedstock does not have to be water washed.

While the invention has been described by specific examples and embodiments, there is no intent to limit the inventive concept except as set forth in the following claims.

We claim:

1. A multistage process for etherifying a mixed $C_4$+ olefinic hydrocarbon feedstock containing isoalkene, comprising:

contacting the olefinic feedstock and aliphatic alcohol in a first reaction stage under partial etherification conditions with a regenerable inorganic metal oxide acid solid catalyst to convert a major amount of the isoalkene to $C_5$+ tertiary-alkyl ether;

recovering a reactant effluent from the first stage containing ether product, unreacted alcohol and unreacted olefin including isoalkene;

charging the first stage effluent to a second stage catalytic distillation column containing solid acid resin etherification catalyst in a plurality of fixed bed catalysis-distillation zones to complete substantially full etherification of isoalkene;

recovering $C_5$+ ether as a liquid from the catalytic distillation column;

regenerating the first stage catalyst to remove feedstock impurity and coke and to restore acid activity; and continuing ether production with regenerated catalyst.

2. The process of claim 1 wherein the alcohol consists essentially of methanol, the first stage catalyst comprises medium pore zeolite and the second stage catalyst comprises polymeric sulfonic acid resin.

3. The process of claim 1 wherein the mixed olefin feedstock consists predominantly of $C_4$ hydrocarbons containing isobutene.

4. The process of claim 1 wherein the first stage comprises a plurality of fixed bed catalyst zones operatively connected for swing from production mode to regeneration mode in alternating sequence.

5. The process of claim 1 wherein the first stage comprises a fluidized bed reaction zone for maintaining a solid particulate acid catalyst, and further including the steps of withdrawing a portion of the solid particulate catalyst from etherification production for regeneration; oxidatively regenerating the solid particulate catalyst at elevated temperature to remove inactivating impurities and coke and to restore acid activity; and returning regenerated catalyst to ether production.

6. The process of claim 1 wherein the mixed olefin feedstock contains impurity selected from nitrogen compounds; Al, Fe, Na and/or Mg metal; butadiene, isoprene or cyclopentadiene.

7. The process of claim 1 wherein the first reaction stage concurrently removes feedstock impurities.

8. The process of claim 1 wherein the first stage comprises at least two serial reactor zones wherein a first reactor zone is maintained at least 5° C. higher than a second reactor zone.

9. The process of claim 1 wherein the second stage catalytic distillation column reaction zone operates at a temperature about 10°–30° C. lower than the first stage.

10. The process of claim 1 wherein the aliphatic alcohol comprises methanol, ethanol or isopropanol.

11. A continuous multistage process for preparing methyl tert-butyl ether comprising:

maintaining two reaction zones in series arrangement, a first reaction zone containing solid crystalline acid medium pore metallosilicate catalyst particles and a second reaction zone containing acid resin catalyst;

contacting a mixed feedstock comprising methanol and isobutene-containing $C_4$ hydrocarbons with the solid metallosilicate catalyst particles in the first reaction zone under etherification conditions to obtain an intermediate product comprising methyl t-butyl ether and unreacted feedstock;

withdrawing intermediate product from first reaction zone; and contacting intermediate product with acid resin catalyst in the second zone under etherification conditions to obtain a product comprising a major amount of methyl t-butyl ether.

12. A process according to claim 11 further comprising the steps of withdrawing the product comprising a major amount of ether from the second reaction zone;

subjecting the product to fractionation to obtain a purified ether; and recovering purified ether.

13. A process according to claim 12 further comprising the steps of removing first reaction zone from on-line contact with feedstock;

regenerating the solid catalyst particles in the first reaction zone; and resuming addition of feedstock to the first reaction zone.

14. A process according to claim 11 wherein the solid acid catalyst particles comprise aluminosilicate zeolite having the structure of ZSM-5, ZSM-11, ZSM-50 or zeolite Beta.

15. A process according to claim 11 wherein the acid resin catalyst comprises a macroreticular polystyrenesulfonic acid catalyst.

16. In a process for preparing an ether by reacting an olefinic feedstock with an alcohol in the liquid phase, in the presence of a solid etherification catalyst of the sulfonic resin type in acid form, wherein the olefinic feedstock contains impurities which substantially reduce the activity of the resin catalyst, the improvement comprising: adding a preliminary step of contacting the olefin and alcohol reactants in the liquid phase with oxidatively regenerable solid acid catalyst particles in a preliminary reaction zone under partial etherification conditions to produce an intermediate stream comprising tertiary-alkyl ether and unreacted olefin and alcohol, said intermediate stream being substantially free of impurities which reduce catalyst activity.

17. A process according to claim 16 wherein the acid catalyst is aluminosilicate having the structure of ZSM-5 or zeolite Beta.

18. A process according to claim 16 wherein the preliminary step is conducted in a swing reactor or slurry type reactor.

19. A process according to claim 16 wherein the olefinic feedstock comprises isobutene in an amount of at least 10 wt. %.

20. A process according to claim 16 wherein the solid catalyst is removed from contact with reactants and regenerated at elevated temperature.

21. A process according to claim 16 wherein solid catalyst zeolite catalyst particles are regenerated by stripping with a hot stream of hydrogen gas at a temperature of about 700° F. to 1000° F.

22. A multistage process for etherifying olefinic hydrocarbon feedstock containing isoamylene, comprising:

contacting the olefinic feedstock and aliphatic alcohol in a first reaction stage under partial etherification conditions with a regenerable inorganic metal oxide acid solid catalyst to convert a major amount of the isoamylene to $C_6^+$ tertiary-amyl ether;

recovering a reactant effluent from the first stage containing ether product, unreacted alcohol and unreacted olefin including isoalkene;

charging the first stage effluent to a second stage catalytic distillation column containing solid acid resin etherification catalyst in a plurality of fixed bed catalysis-distillation zones to complete substantially full etherification of isoamylene;

recovering $C_6^+$ ether as a liquid from the catalytic distillation column;

regenerating the first stage catalyst to remove feedstock impurity and coke and to restore acid activity; and continuing ether production with regenerated catalyst.

23. The process of claim 22 wherein the alcohol consists essentially of methanol, the first stage catalyst comprises medium pore zeolite and the second stage catalyst comprises polymeric sulfonic acid resin.

24. The process of claim 22 wherein the first stage comprises at least two serial reactor zones wherein a first reactor zone is maintained at least 50° C. higher than a second reactor zone; and wherein the second stage catalytic distillation column reaction zone operates at a temperature about 10°–30° C. lower than the first stage.

25. The process of claim 22 wherein the aliphatic alcohol comprises methanol, ethanol or isopropanol.

26. A continuous multistage process for preparing methyl tert-amyl ether comprising:

maintaining two reaction zones in series arrangement, a first reaction zone containing solid crystalline acid medium pore metallosilicate catalyst particles and a second reaction zone containing acid resin catalyst;

contacting a mixed feedstock comprising methanol and isoamylene-containing hydrocarbons with the solid metallosilicate catalyst particles in the first reaction zone under etherification conditions to obtain an intermediate product comprising methyl t-amyl ether and unreacted feedstock;

withdrawing intermediate product from first reaction zone; and contacting intermediate product with acid resin catalyst in the second zone under etherification conditions to obtain a product comprising a major amount of methyl t-amyl ether.

27. A process according to claim 26 wherein the solid acid catalyst particles comprise aluminosilicate zeolite having the structure of ZSM-5, ZSM-11, ZSM-50 or zeolite Beta.

28. A process according to claim 26 wherein the acid resin catalyst comprises a macroreticular polystyrenesulfonic acid catalyst.

* * * * *